US012569303B2

(12) United States Patent
Lenzenhuber et al.

(10) Patent No.: US 12,569,303 B2
(45) Date of Patent: Mar. 10, 2026

(54) SYSTEM AND METHOD FOR MONITORING AT LEAST ONE MEDICAL DEVICE

(71) Applicant: Aesculap AG, Tuttlingen (DE)

(72) Inventors: Frederick Lenzenhuber, Tuttlingen (DE); Roland-Alois Hoegerle, Tuttlingen (DE)

(73) Assignee: Aesculap AG, Tuttlingen (DE)

( * ) Notice: Subject to any disclaimer, the term of this patent is extended or adjusted under 35 U.S.C. 154(b) by 35 days.

(21) Appl. No.: 18/693,247

(22) PCT Filed: Sep. 19, 2022

(86) PCT No.: PCT/EP2022/075973
§ 371 (c)(1),
(2) Date: Mar. 19, 2024

(87) PCT Pub. No.: WO2023/041785
PCT Pub. Date: Mar. 23, 2023

(65) Prior Publication Data
US 2024/0382269 A1 Nov. 21, 2024

(30) Foreign Application Priority Data
Sep. 20, 2021 (DE) ..................... 10 2021 124 194.4

(51) Int. Cl.
*A61B 34/20* (2016.01)
*G16H 40/67* (2018.01)
(52) U.S. Cl.
CPC ............. *A61B 34/20* (2016.02); *G16H 40/67* (2018.01); *A61B 2034/2051* (2016.02)
(58) Field of Classification Search
CPC . A61B 34/20; A61B 2034/2051; A61B 90/98; G16H 40/67; G16H 40/63; G16H 40/20
See application file for complete search history.

(56) References Cited

U.S. PATENT DOCUMENTS 8,449,460 B2 * 5/2013 Duke ................. A61B 17/3462
600/208
9,226,686 B2 * 1/2016 Blair ................ G06K 19/07773
(Continued)

FOREIGN PATENT DOCUMENTS

CN 107072747 A 8/2017
CN 111899859 A 11/2020
(Continued)

OTHER PUBLICATIONS

Search Report received in German Application No. 10 2021 124 194.4 dated Aug. 23, 2022, with translation, 14 pages.
(Continued)

*Primary Examiner* — Daryl C Pope
(74) *Attorney, Agent, or Firm* — Christopher A. Rothe; CM Law

(57) ABSTRACT

A system and method are used for monitoring at least one medical device in a surgical environment. The system includes monitoring apparatuses that can be interconnected for data transmission in a monitoring network and that have a detection device designed to detect whether a transponder of a medical device is located in a detection region extending around the relevant monitoring apparatus. The monitoring apparatuses are arrangeable such that the detection regions overlap. The system also includes a data processing apparatus that is connectable via the monitoring network to the monitoring apparatuses for data transmission and that is designed to store points in time of detections of the transponder. The data processing apparatus can calculate time periods in which the transponder is located exclusively in one of the detection regions and/or to register sequences in which the monitoring apparatuses detect the transponder in the detection regions.

15 Claims, 9 Drawing Sheets

(56)                        References Cited

U.S. PATENT DOCUMENTS

| | | | |
|---|---|---|---|
| 10,709,521 B2 | 7/2020 | Hansen et al. | |
| 11,065,080 B2 * | 7/2021 | Black | A61B 90/53 |
| 2007/0103303 A1 | 5/2007 | Shoarinejad | |
| 2012/0313759 A1 | 12/2012 | Markwitz et al. | |
| 2013/0088354 A1 * | 4/2013 | Thomas | A61B 90/98 |
| | | | 340/572.1 |
| 2017/0224438 A1 | 8/2017 | Johnson et al. | |
| 2019/0151044 A1 | 5/2019 | Black | |
| 2019/0298478 A1 | 10/2019 | Aquino et al. | |
| 2020/0043603 A1 | 2/2020 | Hanajima | |
| 2022/0096163 A1 | 3/2022 | Payyavula et al. | |
| 2024/0138955 A1 | 5/2024 | Black | |

FOREIGN PATENT DOCUMENTS

| | | | |
|---|---|---|---|
| CN | 113366583 A | 9/2021 | |
| DE | 102006042547 A1 | 3/2008 | |
| EP | 2200249 A1 | 6/2010 | |
| EP | 3207491 B1 | 8/2017 | |
| JP | 2019171064 A1 | 10/2019 | |
| JP | 6980753 B2 | 11/2021 | |
| JP | 2022057614 A | 4/2022 | |

OTHER PUBLICATIONS

Search Report received in International Application No. PCT/EP2022/075973 dated Nov. 29, 2022, with translation, 5 pages.
Written Opinion received in International Application No. PCT/EP2022/075973 dated Nov. 29, 2022, with translation, 14 pages.
Office Action received in Chinese Application No. 202280062423.9 dated Jun. 29, 2024, with translation, 16 pages.
Notice of Allowance received in Japanese Application No. 2024-517499 dated Sep. 24, 2024, with translation, 2 pages.

\* cited by examiner

2

4

6

8

1

SYSTEM AND METHOD FOR MONITORING AT LEAST ONE MEDICAL DEVICE

CROSS-REFERENCE TO RELATED APPLICATIONS

This application is the United States national stage entry of International Application No. PCT/EP2022/075973, filed on Sep. 19, 2022, and claims priority to German Application No. 10 2021 124 194.4, filed on Sep. 20, 2021. The contents of International Application No. PCT/EP2022/075973 and German Application No. 10 2021 124 194.4 are incorporated by reference herein in their entireties.

FIELD

The present invention relates to a system for monitoring at least one medical product, in particular to a system for monitoring at least one, in particular reusable, medical product, in particular a surgical instrument, and/or a surgical branch instrument, comprising at least two monitoring devices connected or connectible to each other in a data transmitting manner, in particular wirelessly, in a monitoring network and each comprising a detection device configured to detect whether a transponder of the medical product is located in a detection region extending around the respective monitoring device, wherein the at least two monitoring devices are arranged or arrangeable such that the detection regions of the at least two monitoring devices overlap and a data processing device connected or connectible in a data transmitting manner to the at least two monitoring devices via the monitoring network, in particular wirelessly, and which is configured to be able to store time points of detections of the transponder by the monitoring devices. The present invention further relates to a method for monitoring at least one medical product in a surgical environment.

BACKGROUND

A generic system for monitoring a medical product is disclosed, for example, in U.S. Pat. No. 10,709,521 B2. In the system according to U.S. Pat. No. 10,709,521 B2, medical products are each equipped with two transponders. An identification transponder is configured to return an identification signal in response to an incoming signal. A simple transponder is configured to return a simple signal without identification information in response to an incoming signal. After use in a treatment, the medical products are placed in shielded containers according to U.S. Pat. No. 10,709,521 B2. In the course of treatment, a signal is emitted in specific phases to elicit responses from identification transponders, and a signal is emitted in a specific phase to elicit responses from simple transponders. If reactions from transponders are registered in the phases, this means that medical products have not yet been placed in the shielded containers and are still inside a treated person during an operation, for example.

The problem with the system according to U.S. Pat. No. 10,709,521 B2 is that monitoring of an individual medical product is only insufficiently possible.

SUMMARY

The object of the present disclosure is therefore to provide a system for monitoring at least one medical product, which enables improved monitoring of a medical product, in particular with respect to different application and/or storage area.

A system according to the disclosure for monitoring at least one medical product comprises at least two monitoring devices. The at least two monitoring devices are connected or connectible to each other in a monitoring network in a data transmitting manner, wirelessly or respectively not wired, in particular by radio, or wired. In particular, the at least two monitoring devices may also be connected or connectible to each other in a current-conducting manner. The at least two monitoring devices each have a detection device that is configured to be able to detect whether a transponder of the medical product is located in a detection region extending around the respective monitoring device. The at least two monitoring devices are arranged or arrangeable such that the detection regions of the at least two monitoring devices overlap, that is, that there may be points or regions in the vicinity of the at least two monitoring devices that are located both in the detection region of one of the at least two monitoring devices and in the detection region of the other one of the at least two monitoring devices. The system according to the disclosure comprises a data processing device which is connected or connectible to the at least two monitoring devices via the monitoring network in a data transmitting manner, wirelessly or respectively not wired, in particular by radio, or wired. In particular, the data processing device may also be connected or connectible to the at least two monitoring devices in a current-conducting manner. The data processing device is configured to be able to store time points of detections of the transponder by the monitoring devices. This means that each time one of the at least two monitoring devices transmits a signal to detect a transponder and receives a corresponding response signal from the transponder, the data processing device is configured to store a time stamp for this process. In particular, the data processing device stores in the time stamps an identification of the monitoring device, an identification of the transponder and a time point of receiving the response signal.

According to the disclosure, the data processing device is configured to calculate or, respectively, to be able to calculate time periods in which the transponder is located exclusively in one of the detection regions of the at least two monitoring devices on the basis of stored time points. This means, the data processing device is configured in particular to match or respectively to be able to match the time points or respectively time stamps of individual detections or respectively detection processes of the transponder or respectively of a specific transponder by the at least two monitoring devices, and to separate or respectively to be able to separate those time points or respectively time stamps in which the transponder or respectively a specific transponder is only detected by one of the at least two monitoring devices. The data processing device is furthermore configured in particular to sort out or respectively to be able sort out from these separated time points or respectively time stamps those successive time points or respectively time stamps which are representative of time periods in which the transponder or respectively a specific transponder is located only in the detection region of one of the at least two monitoring devices. The data processing device is configured in particular to calculate or respectively to be able to calculate the time period of successive time points or respectively time stamps by subtracting the oldest time point or respectively time stamp from the most recent time point or respectively time stamp.

Additionally or alternatively, the data processing device is configured to be able to register sequences in which the at least two monitoring devices detect the transponder in the detection regions. In particular, the data processing device may be configured to be able to detect, by comparing data from the at least two monitoring devices, whether the transponder is located exclusively in a single one of the detection regions in the context of an event of a first type or simultaneously in several of the detection regions in the context of an event of a second type, and to be able to store at least one event of the first type and at least one event of the second type in a list. In particular, the events can be stored with associated time data in such a way that the events are arranged in a chronological order.

By calculating time periods and/or registering sequences, it is advantageously possible to carry out monitoring of a medical product more coherently. By calculating the time periods in which the transponder is located in only one detection region, an occupied area of the transponder or respectively of the medical product, in which monitoring is particularly important, can be narrowed down more precisely or more closely by arranging the monitoring devices accordingly.

The border of the respective detection region may be defined by a range of the detection technology used, by a physical border (e.g. the wall of a container) or by a geometric definition (e.g. distance from the detection device).

The system has a memory device in which target time periods and/or target sequences are stored, and the data processing device is configured to compare the calculated time periods with the corresponding target time periods and/or the registered sequences with the target sequences, and to output corresponding alarm signals when target time periods are exceeded and/or when target sequences deviate.

By comparing the calculated time periods with target time periods, the probability of a medical product being used beyond a predetermined service life can be advantageously reduced.

According to one aspect of the disclosure, the medical product may be reusable and/or a surgical instrument. In particular, the medical product may be a non-current-carrying surgical instrument or respectively a surgical instrument without a drive unit of its own.

According to an aspect of the disclosure, the at least two monitoring devices may be configured such that the associated detection regions are of different sizes.

By providing monitoring devices with detection regions of different sizes, monitoring can be adapted in an advantageous manner to differently restricted occupied areas of a medical product. For example, if a medical product is located in an area of a container, the system according to the aspect can be used to efficiently detect whether the medical product is located inside or outside the container by attaching a monitoring device with a comparatively small detection region to the container.

According to an aspect of the disclosure, at least one of the at least two detection devices may be configured to be able to detect or respectively to detect whether the transponder of the medical product is located in a proximity detection region extending around the respective monitoring device and smaller compared to the corresponding detection region and/or may be configured to be able to detect or respectively to detect whether the transponder of the medical product is located in a remoteness detection region extending around the respective monitoring device and larger compared to the corresponding detection region. In other words, at least one of the at least two detection devices may be configured to be able to assign a different remoteness region located in the vicinity of the respective detection device. In particular, one of the at least two detection devices may be configured to be able to vary, in particular cyclically, an intensity of signals that the detection device emits or respectively is able to emit for detecting the transponder.

According to an aspect of the disclosure, the data processing device may be configured to calculate or respectively to be able to calculate time periods in which the transponder is located in the at least one proximity detection region and/or in the at least one remoteness detection region based on the stored time points or respectively time stamps of the detections in the proximity detection region and according to the stored time points or respectively time stamps of the detections in the remoteness detection region.

According to an aspect of the disclosure, the data processing device may be configured to calculate or respectively to be able to calculate time periods in which the transponder is not in the at least one proximity detection region and/or not in the at least one remoteness detection region based on the stored time points or respectively time stamps of the detections in the proximity detection region and according to the stored time points or respectively time stamps of the detections in the remoteness detection region.

By providing an additional proximity detection region and/or an additional remoteness detection region and by calculating corresponding time periods, the spatial resolution of a monitoring may be increased in an advantageous way.

According to one aspect of the disclosure, at least one of the detection devices may be configured to be able to emit or respectively to emit electromagnetic waves, in particular radio waves, of a first frequency band, in particular with a frequency between 860 MHz and 950 MHz or with a frequency between 2.45 GHz and 6 GHz, in particular between 2.45 GHz and 5.8 GHz, for detecting the transponder and to be able to receive or respectively to receive them from the transponder, and at least one of the detection devices may be configured to be able to emit or respectively to emit electromagnetic waves, in particular radio waves, of a second frequency band, in particular with a frequency of 13.56 MHz, for detecting the transponder and to be able to receive or respectively to receive them from the transponder. In particular, one of the detection devices may be configured to operate in the first frequency band and another detection device may be configured to operate in the second frequency band. According to the disclosure, a detection device may also be configured to operate in both the first and the second frequency band. In particular, a plurality of detection devices may be provided, each configured to operate in a respective frequency band.

By tuning the detection devices to the first and/or second frequency band, the system according to the disclosure may advantageously be adapted to different environmental conditions and thus different attenuations.

According to one aspect of the disclosure, at least one of the detection devices, in particular the at least one detection device configured to detect the transponder in the remoteness detection region, may be configured to be able to emit or respectively to emit electromagnetic waves, in particular radio waves, according to a first transmission standard, in particular a near field communication standard, for detecting the transponder, in particular in the corresponding detection region, and to be able to receive or respectively to receive them from the transponder, and at least one of the detection devices, in particular the at least one detection device configured to detect the transponder in the remoteness detection region, may be configured to be able to emit or respectively to emit electromagnetic waves, in particular radio waves, according to a second transmission standard, in particular an RFID transmission standard, for detecting the transponder, in particular in the corresponding remoteness detection region, and to be able to receive or respectively to receive them from the transponder. In particular, one of the detection devices may be configured to operate in the first transmission standard and another detection device may be configured to operate in the second transmission standard and thus realize in particular detection regions of different sizes. According to the disclosure, a detection device, in particular the at least one detection device configured to detect the transponder in the remoteness detection region, may also be configured to be operated in both the first and the second transmission standard. In particular a detection device may be configured to detect the transponder or respectively a transponder in the detection region on the basis of the first transmission standard and to detect it in the proximity detection region and/or remoteness detection region on the basis of the second transmission standard.

If detection devices are operated according to known transmission standards, it is advantageously possible to integrate conventional reading devices into a system according to the disclosure. For example, a smartphone may be converted into a detection device according to the disclosure or respectively into a monitoring device according to the disclosure by programming it to detect a transponder using a near-field communication standard.

According to one aspect of the disclosure, the monitoring network may be configured to be operated according to a third transmission standard, in particular a WLAN standard according to IEEE 802.11 or a WPAN standard according to IEEE 802.15 such as Bluetooth®, or according to Bluetooth® Low Energy (BLE).

If the monitoring network is operated in a standard that differs from the standards for detecting the transponder, interacting interference can be prevented or at least reduced in an advantageous way.

According to an aspect of the disclosure, the monitoring network may be partially or fully meshed. In particular, a plurality of monitoring devices may each be provided with data processing units, each of which may receive and store the time periods calculated by the data processing device from the data processing device.

The meshed configuration of the monitoring network allows data communication to continue if a monitoring device or connection fails by rerouting the data communication.

According to an aspect of the disclosure, the system may have a memory device in which target time periods and/or target sequences are stored, and the data processing device may be configured to be able to compare the calculated time periods with the corresponding target time periods and/or the registered sequences with the target sequences, and to be able to output corresponding alarm signals when target time periods are exceeded and/or when target sequences deviate.

By comparing the calculated time periods with target time periods, the probability of a medical product being used beyond a predetermined service life can be advantageously reduced.

According to an aspect of the disclosure, at least one monitoring device may be arranged in a sterile goods container, or respectively the system according to the disclosure may comprise at least one sterile goods container equipped with a monitoring device.

According to an aspect of the disclosure, at least one monitoring device may be arranged in a storing region of a surgical environment, at least one monitoring device may be arranged in the surgical environment in a sterile region at a side table in the vicinity of a surgical table, and at least one monitoring device may be arranged in the surgical environment in the sterile region at the surgical table. The storing region is in particular further away from the surgical table than the side table. The sterile region is in particular an area extending around the surgical table and its borders are at least one meter away from the surgical table.

Improved, in particular seamless, monitoring can be made possible by arranging the monitoring devices in a sterile goods container and/or in regions that are traversed during use of a medical product.

According to an aspect of the disclosure, a system according to the disclosure may comprise a positioning system configured to be able to detect and/or register relative positions of the at least two monitoring devices. In particular, the positioning system may comprise sensors capable of detecting the positions of the at least two monitoring devices. Alternatively or additionally, the monitoring devices may have interfaces to a global navigation satellite system, such as NAVSTAR GPS or Galileo, via which the respective monitoring device can determine its own position, and the monitoring devices may be configured to be able to transmit their position to the positioning system, which may be configured to be able to calculate and register relative positions of the monitoring devices from the positions of the monitoring devices. Alternatively or additionally, the positioning system may also be configured in such a way that relative positions of the at least two monitoring devices can be entered via an input device such as a touch-sensitive screen, a keyboard or a mouse and can be registered by the positioning system.

If relative positions of the monitoring devices are taken into account, it is possible to estimate where a medical product is located with a certain probability and whether non-detection of a medical product is critical or not, even if the detection regions of the monitoring devices do not overlap.

The disclosure further relates to a method for monitoring at least one medical product in a surgical environment (for example in an operating room). At least two monitoring devices connected or connectible to each other in a monitoring network in a data transmitting manner are arranged or arrangeable in the surgical environment such that detection regions of the at least two monitoring devices extending around the respective monitoring device overlap. The medical product is in particular reusable and/or a surgical instrument. The method comprises the following steps:

detecting whether a transponder of the medical product is located in one of the detection regions, storing of time points of detections of the transponder, and calculating of time periods in which the transponder is located exclusively in one of the detection regions of the at least two monitoring devices, comparing the calculated periods with corresponding stored target periods and outputting corresponding alarm signals when target periods are exceeded and/or registering sequences in which the at least two monitoring devices detect the transponder in the detection regions comparing the registered sequences with corresponding stored target sequences and outputting corresponding alarm signals in the event of a deviation from target sequences.

The detecting step is carried out in particular by a detection device of the monitoring device associated with the respective detection region. The border of the respective detection region can be defined by a range of a detection technology used, by a physical border (e.g. a wall of a container) or by a geometric definition (e.g. distance from the detection device).

The storing step and/or the calculating step is/are performed in particular by a data processing device connected or connectible to the at least two monitoring devices via the monitoring network in a data transmitting manner.

BRIEF DESCRIPTION OF THE DRAWING FIGURES

The present disclosure is described in more detail below with reference to the accompanying drawings by way of a preferred configuration example. The following is shown:

DETAILED DESCRIPTION

Figure 1:
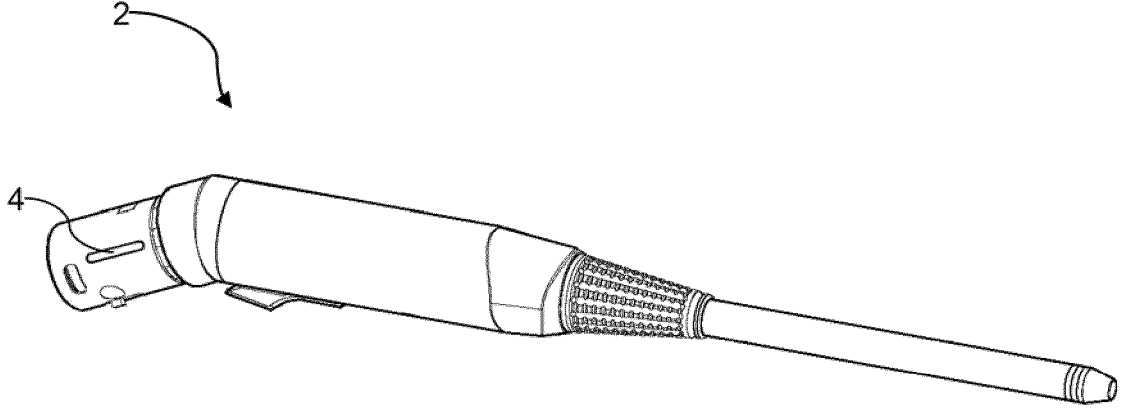
FIG. 1 shows a perspective view of a medical product in the form of a surgical micromotor instrument with a transponder.

FIG. 1 shows a perspective view of a medical product in the form of a surgical micromotor instrument 2 with a transponder 4. The transponder 4 is attached to a connector at a proximal end of the micromotor instrument 2.

Figure 2:
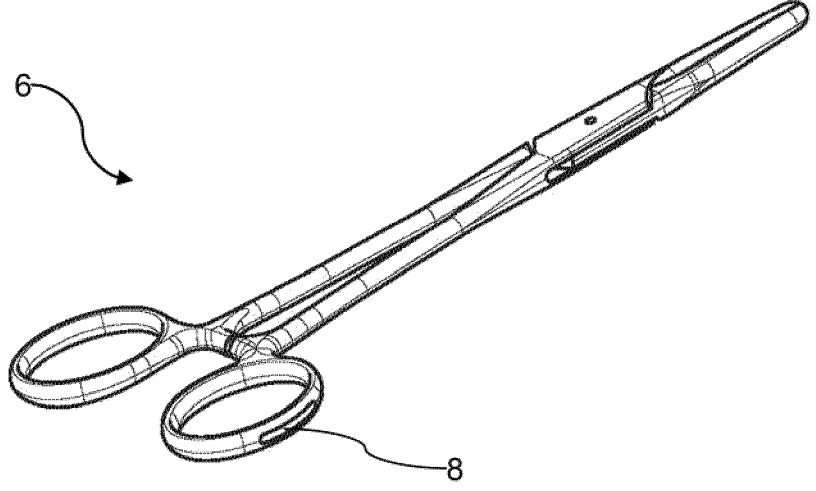
FIG. 2 shows a perspective view of a medical product in the form of a needle holder with a transponder.

FIG. 2 shows a perspective view of a medical product in the form of a needle holder 6 with a transponder 8. The transponder 8 is attached to a ring of a handle opening of the needle holder 6.

The transponders 4 and 8 are each configured to emit a corresponding response signal when receiving signals according to a short-range communication standard and to emit a corresponding (different) response signal when receiving signals according to a (different) RFID standard. The transponders 4 and 8 are thus configured as hybrid tags. The transponders 4 and 8 each have no energy storage of their own and are therefore passively configured. The transponders 4 and 8 only transmit corresponding response signals when receiving predetermined signals. The response signals each contain information that uniquely assigns the response signal to the corresponding transponder 4 or 8 and thus uniquely to the corresponding medical product 2 or 6.

Figure 3:
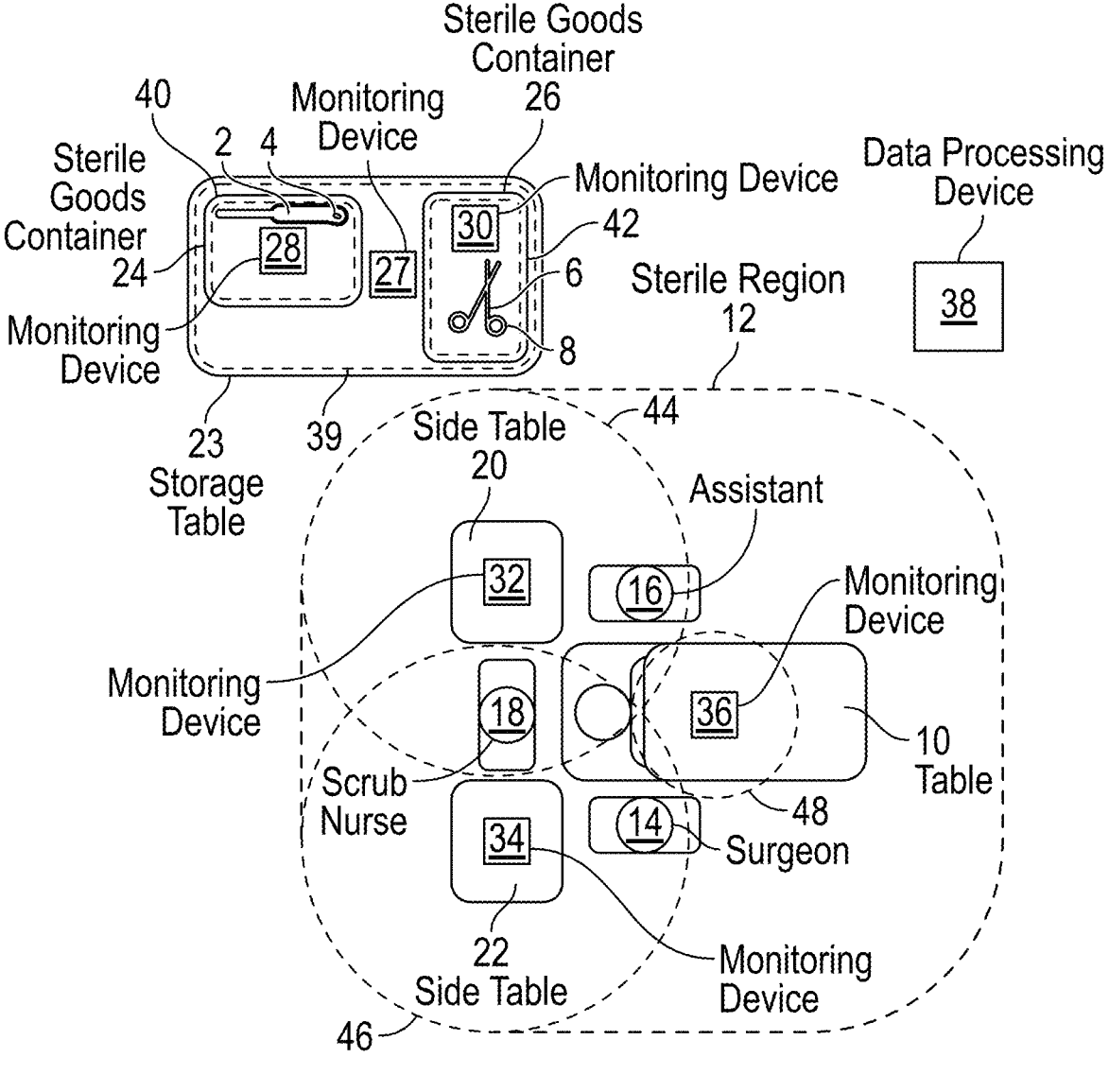
FIG. 3 shows a schematic view of a system according to the disclosure in a state in which medical products are stored in sterile goods containers on a storage table away from a sterile region.

FIG. 3 shows a schematic top view of an operating room equipped with a system according to the disclosure. The operating room has a surgical table 10 around which a sterile region 12 extends. Within the sterile region 12, a surgeon 14, an assistant 16 and a scrub nurse 18 stand around the surgical table 10. Two side tables 20 and 22 are arranged on either side of the scrub nurse 18 standing at one end of the surgical table 10. A storage table 23 is arranged in the operating room away from the sterile region 12. On the storage table 23, the micromotor instrument 2 is stored inside a sterile goods container 24 and the needle holder 6 is stored inside a sterile goods container 26.

A monitoring device 27 is provided on the storage table 23. A monitoring device 28 is provided on or respectively in the sterile goods container 24. A monitoring device 30 is provided on or respectively in the sterile goods container 26. A monitoring device 32 is provided on the instrument table 20. A monitoring device 34 is provided on the instrument table 22. A monitoring device 36 is provided on the surgical table 10. The monitoring devices 27 to 36 are each connected to a data processing device 38 and to each other in a non-wired manner via a standard WLAN network, such as a Bluetooth® network or a BLE network.

A detection region 39, 40, 42, 44, 46 and 48 extends around each of the monitoring devices 27 to 36.

The monitoring device 27 is configured such that borders of the detection region 39 of the monitoring device 27 correspond at least substantially to an outline of the storage table 23. The monitoring device 27 is configured to detect the transponder 4 or respectively 8 via a near field communication signal.

The detection region 40 of the monitoring device 28 and the detection region 42 of the monitoring device 30 are each bounded by the corresponding sterile goods container 24 or respectively 26, in which the micromotor instrument 2 or respectively the needle holder 6 is stored. The monitoring devices 28 and 30 are configured to detect the transponder 4 or respectively 8 via a near field communication signal.

The monitoring devices 32 and 34 are configured to detect the transponder 4 or respectively 8 via an RFID signal. Accordingly, the detection region 44 of the monitoring device 32 and the detection region 46 of the monitoring device 34 are larger than the detection regions 40 and 42.

The monitoring device 36 is also configured to detect the transponder 4 or respectively 8 via an RFID signal. However, the intensity of the RFID signal of the monitoring device 36 is lower than the intensity of the RFID signals of the monitoring devices 32 and 34. Accordingly, the detection region 48 of the monitoring device 36 is smaller than the detection regions 44 and 46 of the monitoring devices 32 and 34.

Figure 4:
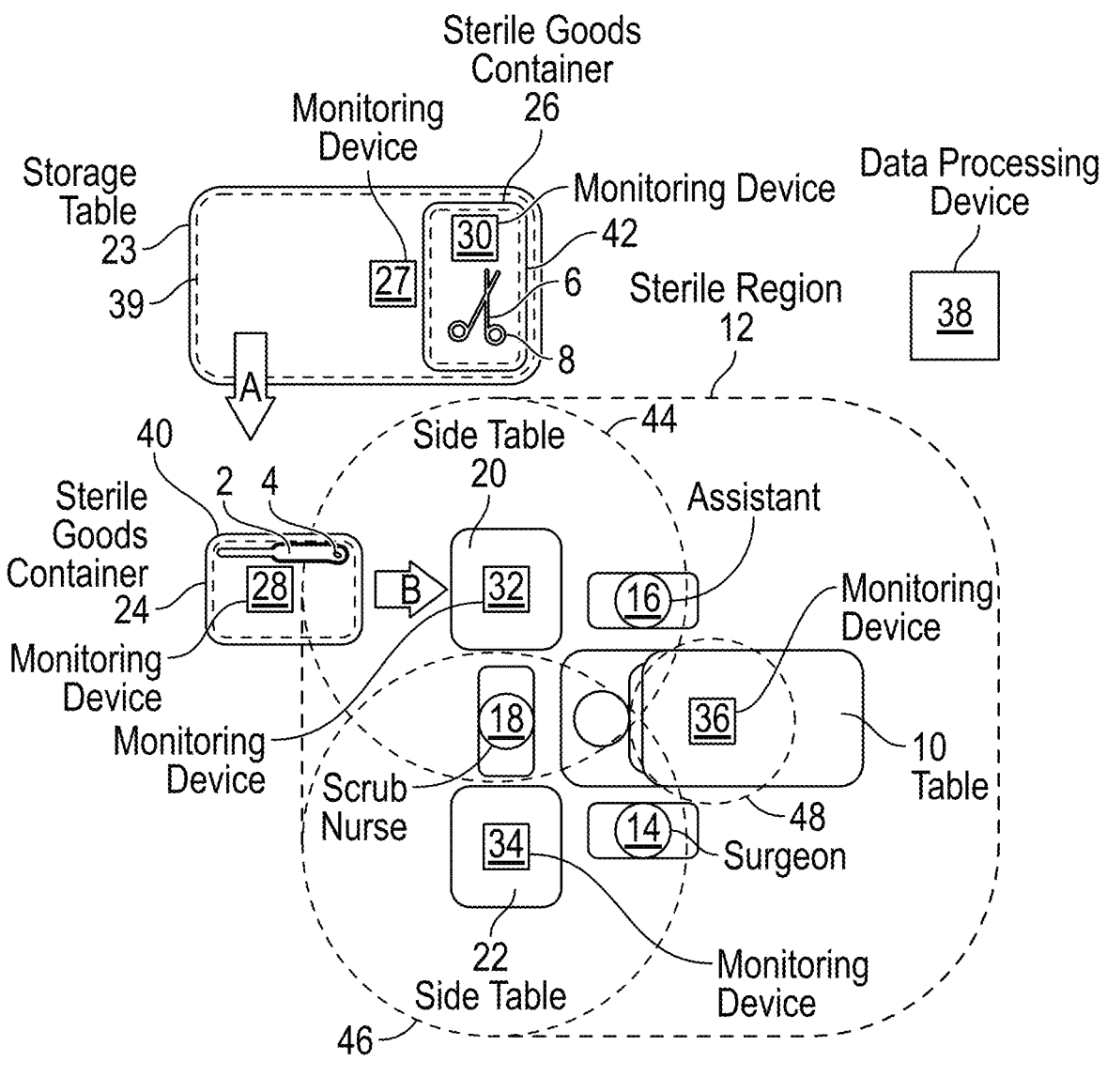
FIG. 4 shows a schematic view of the system according to FIG. 3 in a state in which one of the sterile goods containers is located outside a storage area and partially outside the sterile region.

FIG. 4 shows a schematic view of the system according to FIG. 3 in a state in which the sterile goods container 24 has been removed from the storage table 23 (see arrow A)

and the sterile goods container 24 is located outside a storage area defined by the storage table 23 and partially inside the sterile region 12. In the state shown in FIG. 4, the transponder 4 is located both in the detection region 40 of the sterile goods container 24 and in the detection region 44 of the monitoring device 32 of the side table 20. Since both the monitoring device 28 and the monitoring device 32 detect the transponder 4, the system or respectively the data processing device 38 can detect that the micromotor instrument 2 is still in the sterile goods container 24 and that the sterile goods container 24 is at least partially in the detection region 44 and thus at least partially in the sterile region 12. When the sterile goods container 24 is moved from the edge of the detection region 44 in the direction of the side table 20 (see arrow B), the system or respectively the data processing device 38 does not register any state change, since only the monitoring devices 28 and 32 continue to detect the transponder during such a movement.

In the state shown in FIG. 4, the micromotor instrument 2 and the sterile goods container 24 are no longer on the storage table 23. The transponder 4 is therefore no longer in the detection region 39, but in the detection region 44. The time point from which the transponder 4 is no longer detected by the monitoring device 27 and the transponder 4 is therefore not in the detection region 39 is reported by the monitoring device 27 to the data processing device 38. Similarly, the time point from which the transponder 4 is detected by the monitoring device 32 and the transponder is therefore located in the detection region 44 is reported by the monitoring device 32 to the data processing device 38.

Figure 5:
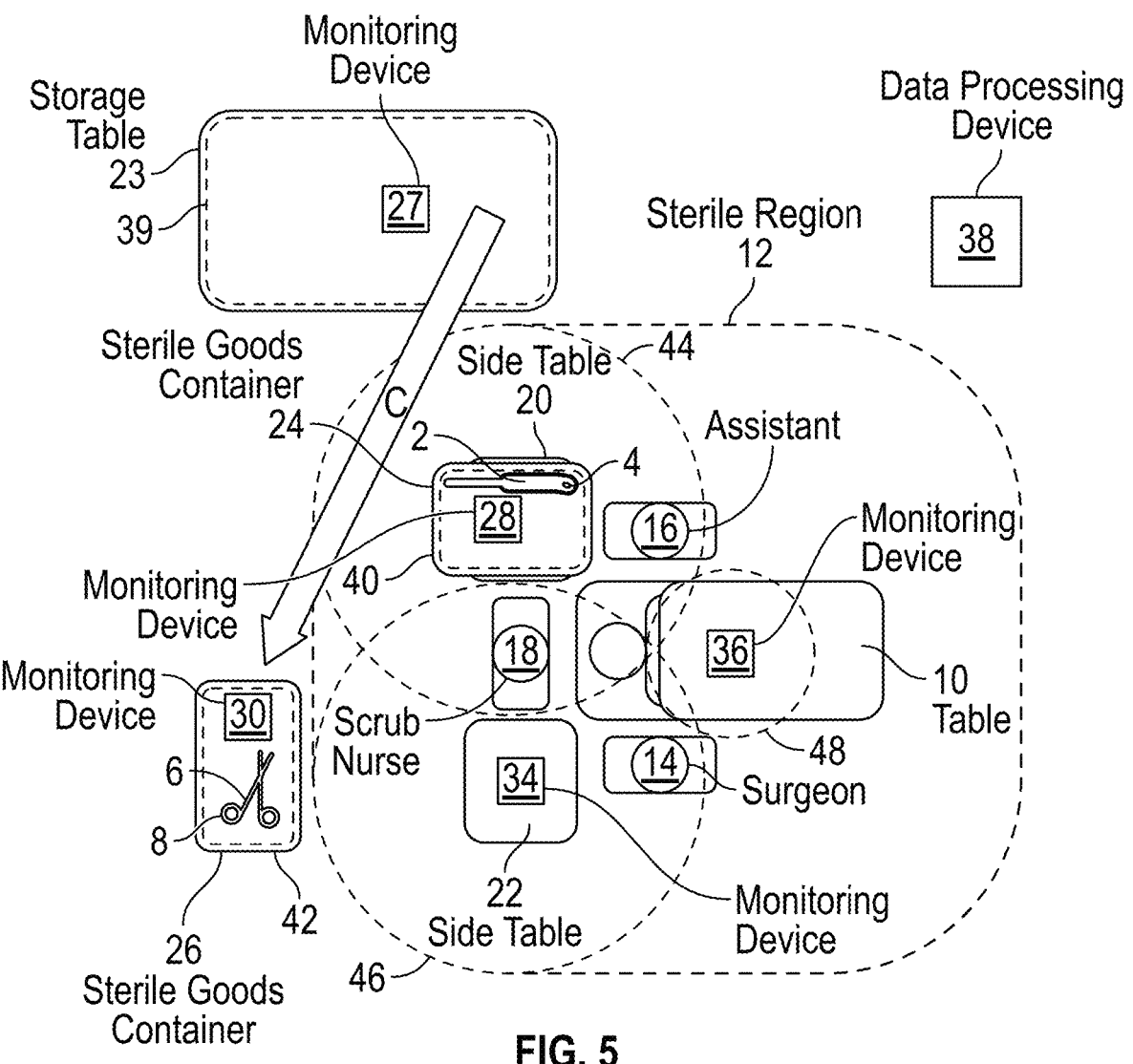
FIG. 5 shows a schematic view of the system according to FIG. 3 in a state in which one of the sterile goods containers is temporarily stored on a side table inside the sterile region and one of the sterile goods containers is located outside the storage area and outside the sterile region.

In the state shown in FIG. 5, the sterile goods container 24 with the micromotor instrument 2 is located on the side table 20. According to the embodiment shown, the data processing device 38 cannot distinguish the state of the micromotor instrument 2 or respectively sterile goods container 24 shown in FIG. 5 from the state shown in FIG. 4. For improved monitoring, the monitoring device 32 may be configured such that it can detect whether a transponder or respectively the transponder 4 is located in a proximity detection region extending around the monitoring device 32, which is smaller than the detection region 44 and extends in particular substantially according to the layout of the side table 20.

Figure 6:
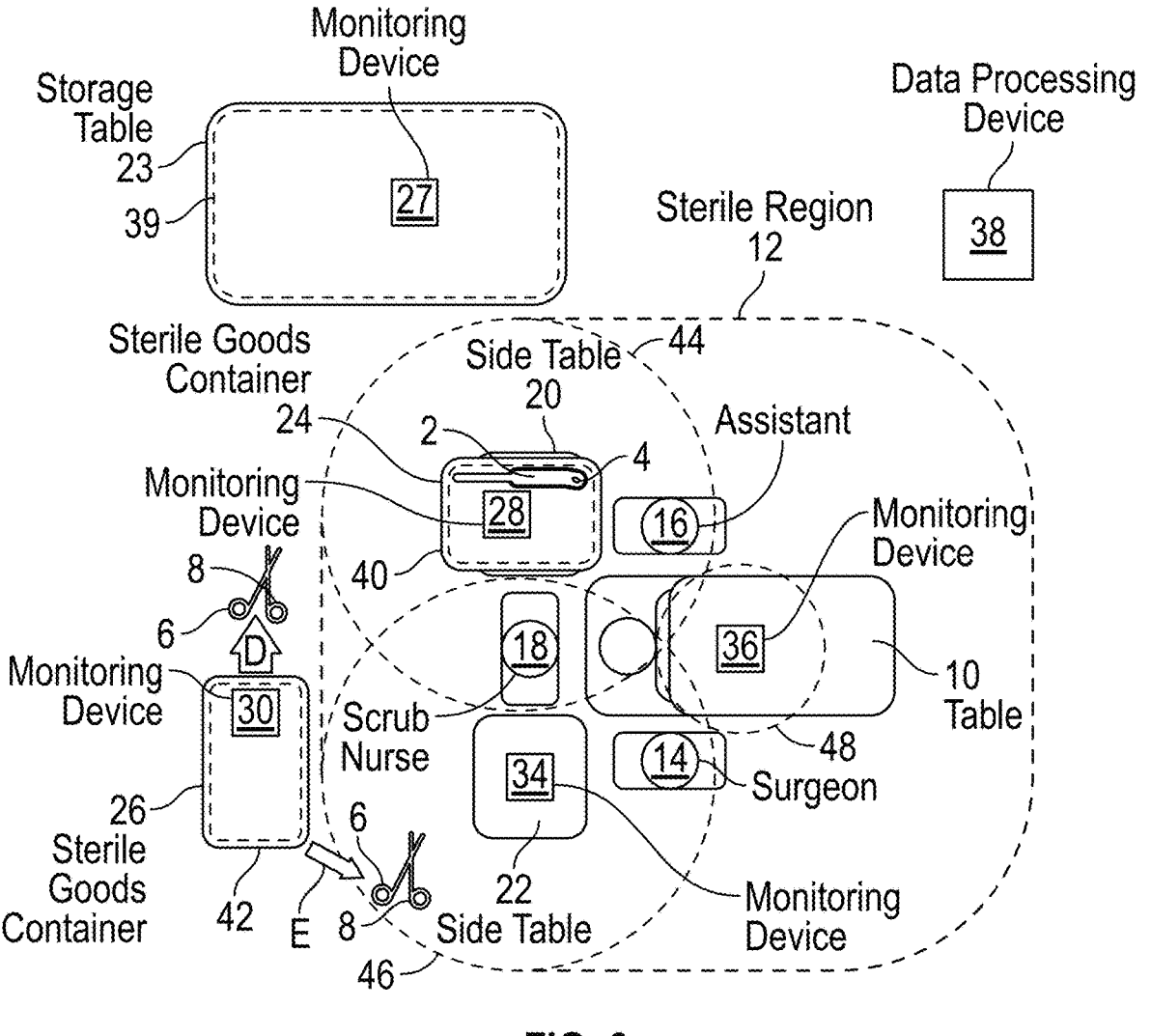
FIG. 6 shows a schematic view of the system according to FIG. 3 in a state in which a medical product, which is taken from the sterile goods container located outside the sterile region, is alternatively located outside or inside the sterile region.

In the state shown in FIG. 5, the sterile goods container 26 is removed from the storage table 23 (see arrow C) and the sterile goods container 26, together with the needle holder 6 and the transponder 8, is located outside the storage area defined by the storage table 23 and outside the sterile region 12. If the needle holder 6 is removed from the sterile goods container 26 in this state (see arrows D and E in FIG. 6), the monitoring device 30 of the sterile goods container 26 reports to the data processing device 38 that it no longer detects the transponder 8 and the data processing device 38 registers the corresponding time point. By matching with data received from the other monitoring devices 27, 28, 34 and 36, the data processing device 38 detects that the needle holder 6 is not detected by any of the monitoring devices 27 to 36 during or respectively immediately after its removal from the sterile goods container arranged outside the storage area and outside the sterile region. The data processing device 38 according to the embodiment is configured to output an alarm and/or a warning in the event of such a disappearance of an already detected transponder 8 from the detection regions 39 to 48. It is irrelevant whether the transponder 8 is detected by another monitoring device, for example by the monitoring device 34 of the side table 22, a short time after disappearing from the detection region 42 (see arrow E in FIG. 6).

Figure 7:
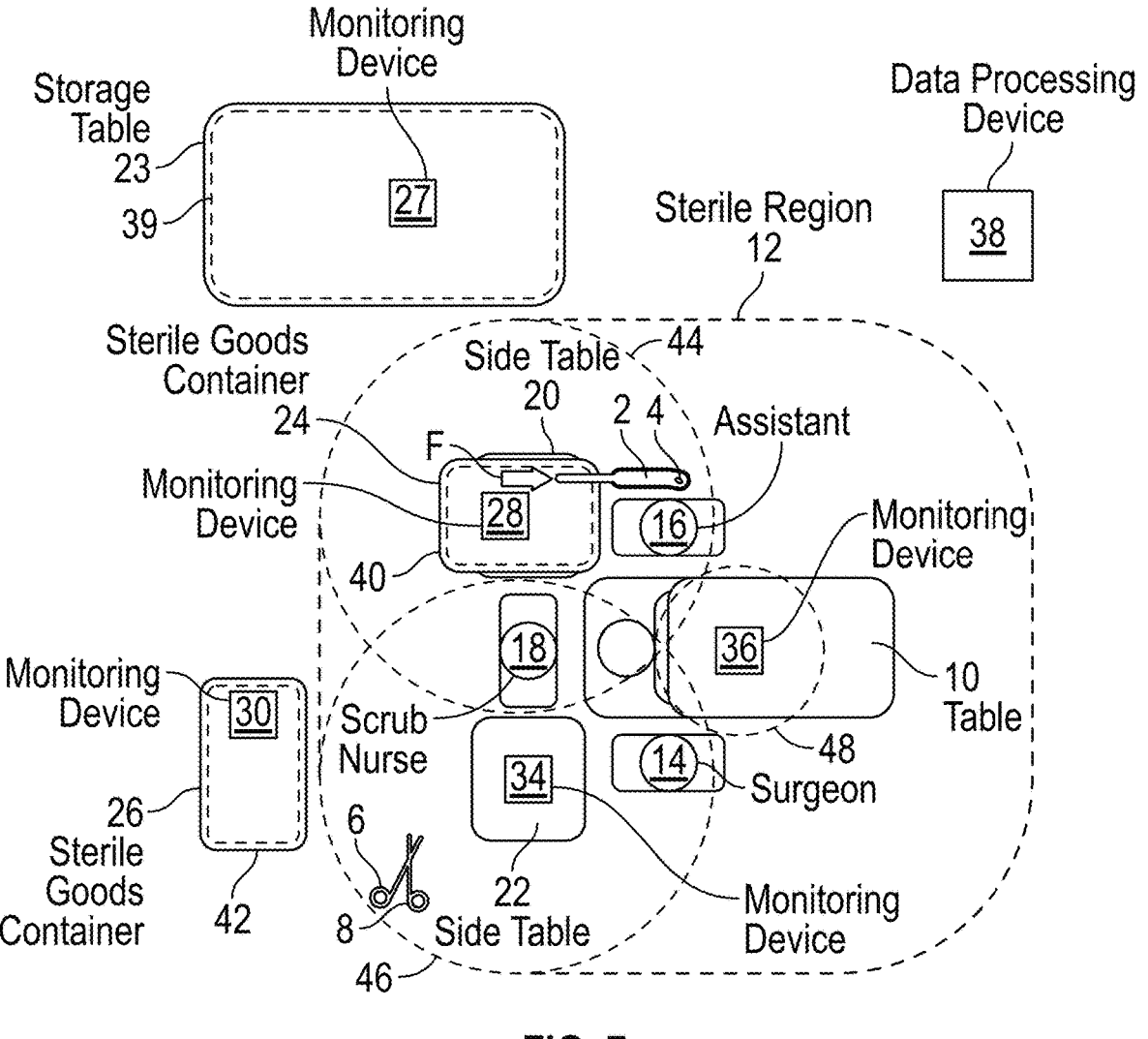
FIG. 7 shows a schematic view of the system according to FIG. 3 in a state in which one of the medical products within the sterile region is removed from the side table but is outside a surgical area.

In the state shown in FIG. 7, the micromotor instrument 2 is removed from the sterile goods container 24 resting on the side table 20 (see arrow F) and the micromotor instrument 2 or respectively the transponder 4 is located exclusively in the detection region 44 of the monitoring device 32 of the side table 20. The detection region 44 of the monitoring device 32 of the side table 20 is configured such that it extends exclusively in the sterile region 12, so that removal of the micromotor instrument 2 within the detection region 44 does not lead to any alarm and/or warning message by the data processing device 38.

Figure 8:
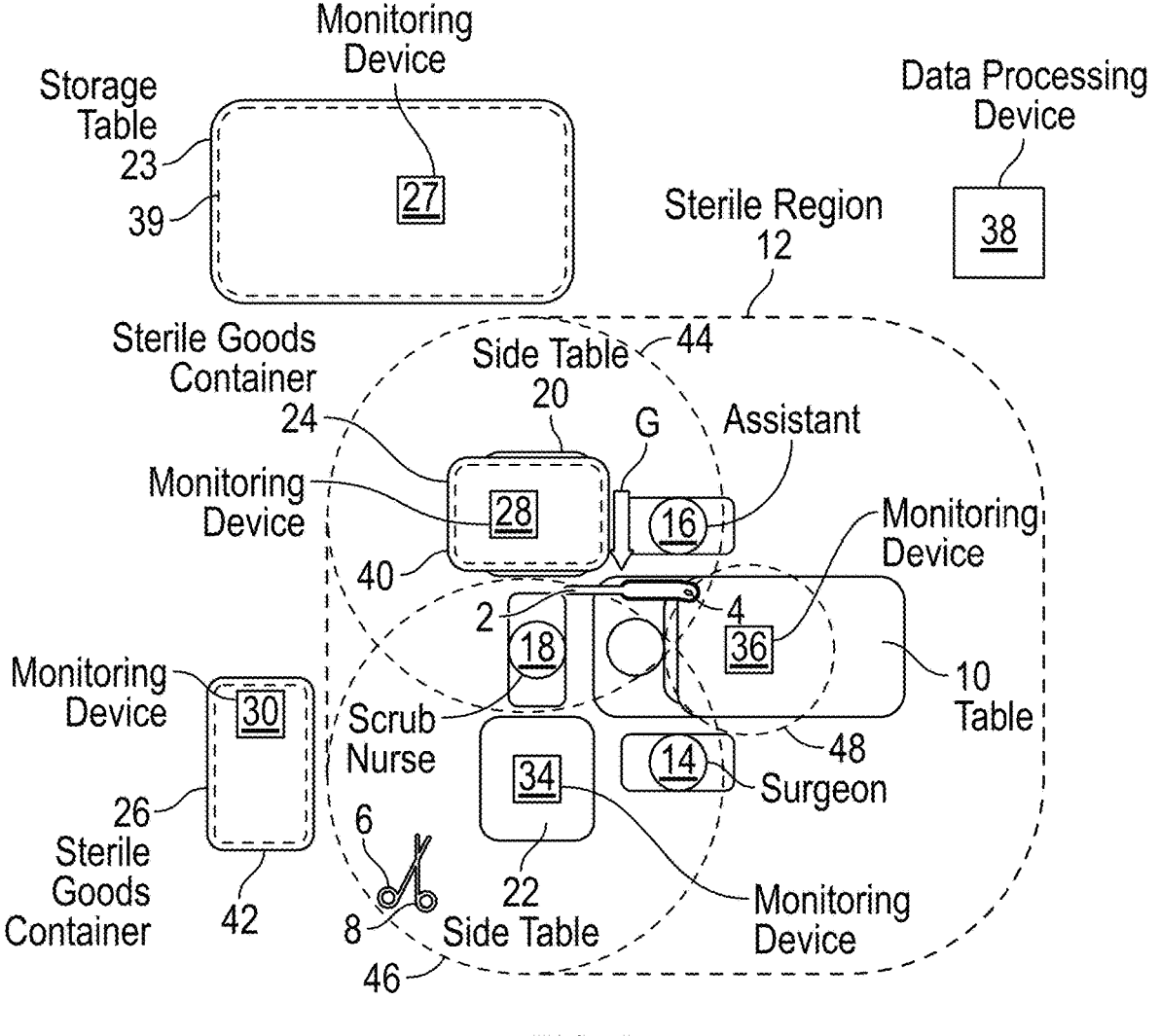
FIG. 8 shows a schematic view of the system according to FIG. 3 in a state in which one of the medical products within the sterile region is removed from the side table and is in the proximity of a surgical area.

In the state shown in FIG. 8, the micromotor instrument 2 has been moved in the direction of the surgical table 10 (see arrow G) and the transponder 4 of the micromotor instrument 2 is located in an overlap area of the detection region 44 of the monitoring device 32 of the side table 20 and the detection region 48 of the monitoring device 36 on the surgical table 10. As soon as the transponder 4 reaches the detection region 48 when moving the micromotor instrument 2 in the direction of the surgical table 10 and is thus detected by the monitoring device 36, the monitoring device 36 reports the corresponding time point to the data processing device 38.

Figure 9:
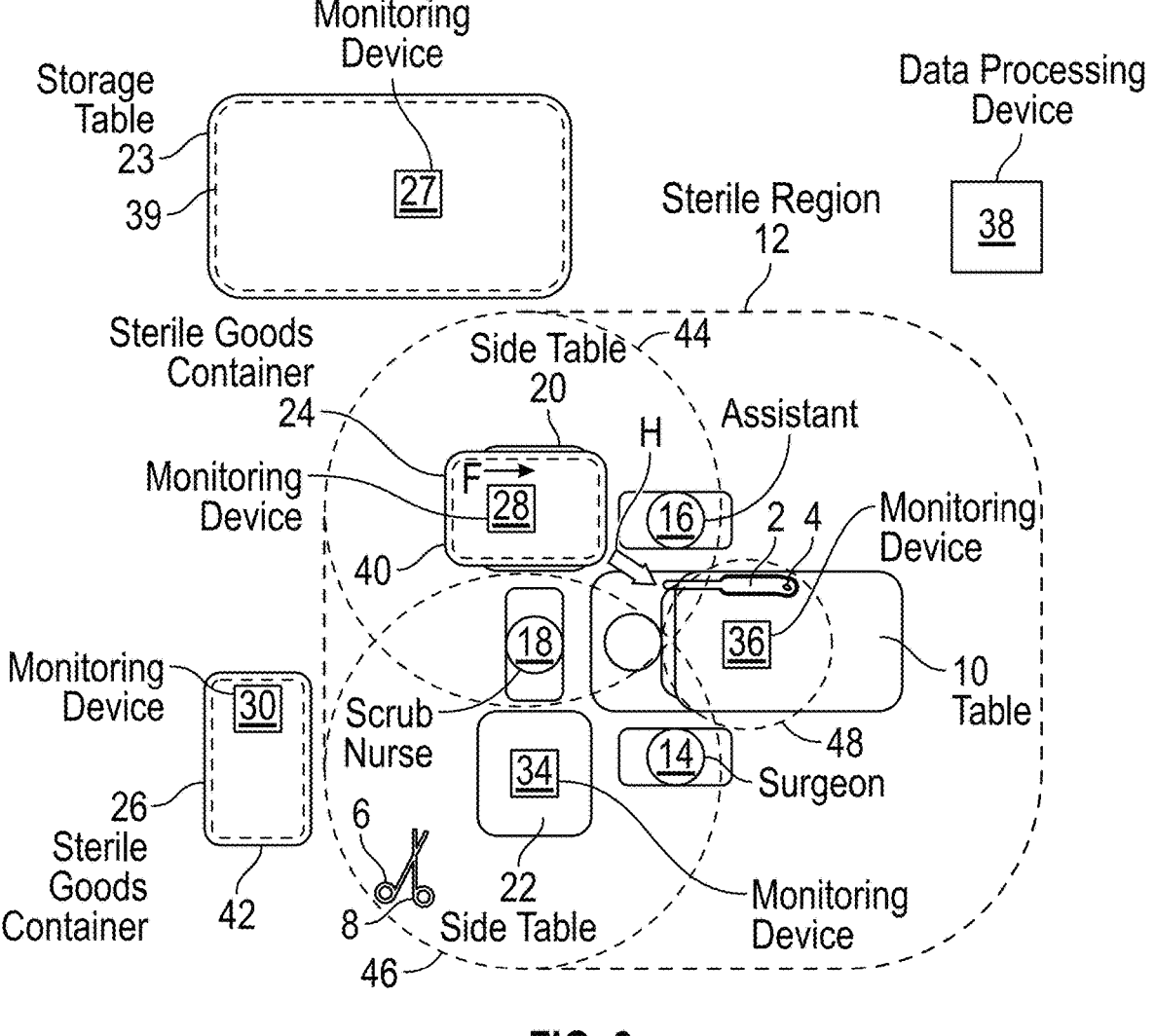
FIG. 9 shows a schematic view of the system according to FIG. 3 in a state in which one of the medical products is located within a surgical area.

In the state shown in FIG. 9, the micromotor instrument 2 has been moved further in the direction of the surgical table 10 (see arrow H) and the transponder 4 of the micromotor instrument 2 is now located exclusively in the detection region 48 of the monitoring device 36 of the surgical table 10. The time point at which the transponder 4 is no longer detected by the monitoring device 32 and the transponder 4 is therefore no longer located in the detection region 44 is reported by the monitoring device 32 to the data processing device 38.

The data processing device 38 can calculate the time periods during which the transponder 4 is located in the respective detection regions 39, 40, 44 and 48 on the basis of the time points of the detections or respectively the no-more-detections of the transponder 4 in the detection regions 39, 40, 44 and 48 reported by the monitoring devices 27, 28, 32 and 36 to the data processing device 38. If the micromotor instrument 2 is moved again in reverse order from the surgical table 10 to the storage table 23, the time points of the transponder detections are reported accordingly to the data processing device 38 by the monitoring devices and the data processing device 38 again calculates the time periods during which the transponder 4 is located in the respective detection region 39, 40, 44 and 48.

The system according to the disclosure shown in FIG. 3 to FIG. 9 makes it possible to calculate the total residence time periods of the micromotor instrument 2 in the individual detection regions 39, 40, 44 and 48 and thus to achieve coherent monitoring of the micromotor instrument 2.

The needle holder 6 can be monitored in the same way as the micromotor instrument 2.

At least one predetermined course of an operation may be stored in the data processing device 38, from which a sequence of at least two instruments to be used for the operation can be derived. If, for example, a micromotor instrument 4 and then a needle holder 8 has to be used first during an operation, the data processing device 38 can output corresponding assistant messages during the operation and/or an alarm or warning message if there is a deviation from the predetermined course, for example if the needle holder 8 is detected by the monitoring device 36 of the surgical table 10 before the micromotor instrument 4. The data processing device 38 may also be configured such that it issues an alarm or warning message if, at the end of an operation, the instruments 2 and 6, in particular the reusable instruments, are not detected by the monitoring devices 28 and 30 in the corresponding sterile goods containers 24 and 26 and/or are not detected by the monitoring device 27 on the storage table 23.

By using a transponder in the form of a hybrid tag, it is easy to provide detection regions of different sizes and thus flexibly design the shape of a monitored area. If only states in which only a single monitoring device detects a transponder are taken into account when calculating time periods, an area with a complex shape can be monitored by overlapping several detection regions of different monitoring devices.

Figure 10:
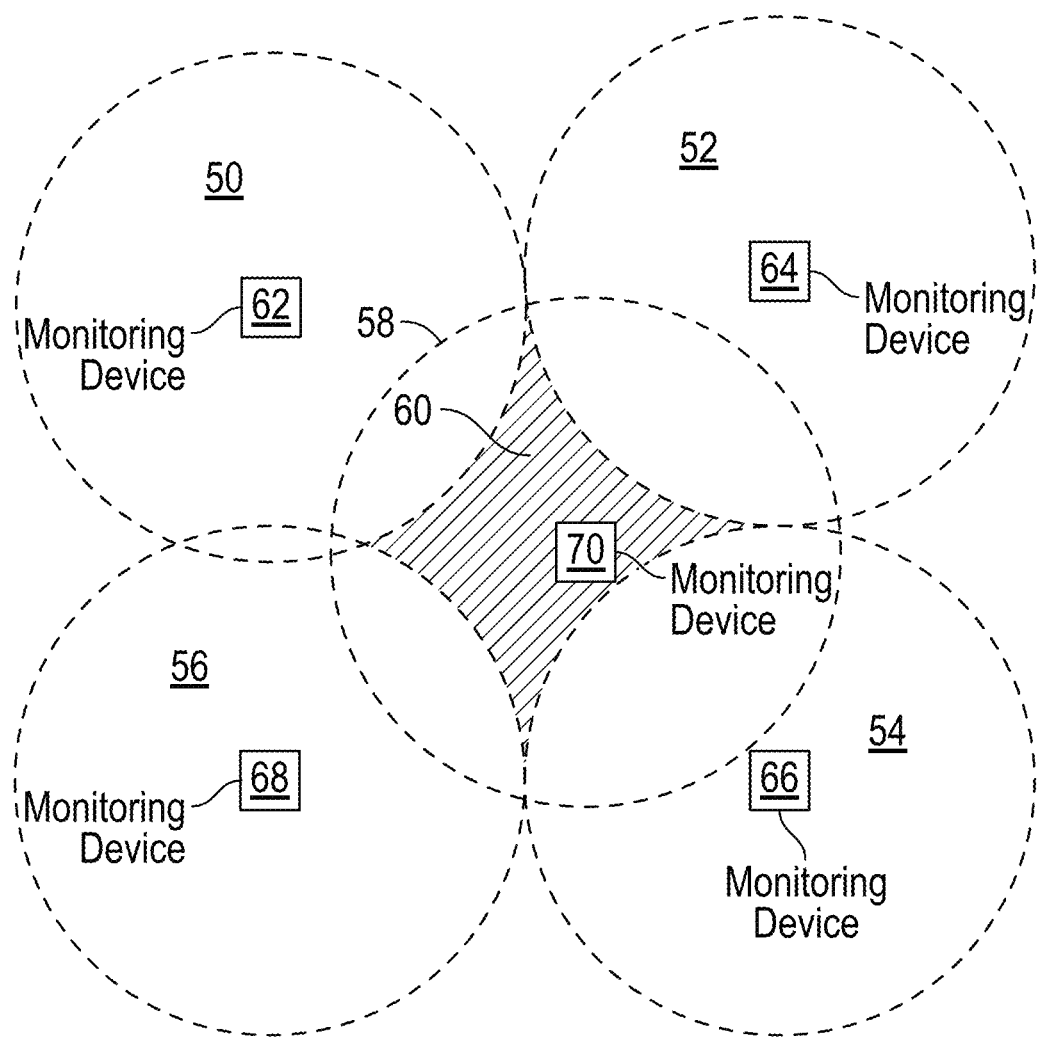
FIG. 10 shows a schematic view of a monitoring region formed by overlapping several detection regions.

FIG. 10 shows a schematic view of a monitoring region 60 formed by overlapping several detection regions 50, 52, 54, 56 and 58. For example, four monitoring devices 62, 64, 66 and 68 are arranged around a central monitoring device 70 in such a way that overlappings of the detection regions 50, 52, 54 and 56 of the externally arranging monitoring devices 62, 64, 66 and 68 with the detection region 58 of the centrally arranging monitoring device 70 delimit a part of the detection region 58 of the centrally arranging monitoring device 70 that does not overlap with any other detection region. The part of the detection region 58 of the centrally arranging monitoring device 70 that does not overlap with any other detection region constitutes the monitoring region 60, in which time periods of a transponder's whereabouts can be calculated according to the disclosure.

The invention claimed is:

1. A system for monitoring at least one medical product, the system comprising:

at least two monitoring devices connected or connectible to each other in a data transmitting manner in a monitoring network and each comprising a detection device configured to detect whether a transponder of the medical product is located in a detection region extending around the respective monitoring device, wherein the at least two monitoring devices are arranged such that the detection regions of the at least two monitoring devices overlap;

a data processing device connected or connectible in a data transmitting manner to the at least two monitoring devices via the monitoring network and which is configured to store time points of detections of the transponder by the monitoring devices; and calculate time periods in which the transponder is located exclusively in one of the detection regions of the at least two monitoring devices, compare the calculated time periods with corresponding target time periods stored in the memory device and to output corresponding alarm signals when target time periods are exceeded, and/or register sequences in which the at least two monitoring devices detect the transponder in the detection regions, to compare the registered sequences with target sequences stored in the memory device and to output corresponding alarm signals when target sequences deviate.

2. The system according to claim 1, wherein the medical product is reusable and/or a surgical instrument.

3. The system according to claim 1, wherein the at least two monitoring devices are configured such that the associated detection regions are of different sizes.

4. The system according to claim 1, wherein at least one of the at least two detection devices is configured to be able to detect whether the transponder of the medical product is located in a proximity detection region extending around the respective monitoring device and smaller compared to the corresponding detection region and/or is configured to be able to detect whether the transponder of the medical product is located in a remoteness detection region extending around the respective monitoring device and larger compared to the corresponding detection region.

5. The system according to claim 4, wherein the data processing device is configured to be able to calculate time periods in which the transponder is located in the at least one proximity detection region and/or in the at least one remoteness detection region.

6. The system according to claim 4, wherein the data processing device is configured to be able to calculate time periods in which the transponder is not in the at least one proximity detection region and/or not in the at least one remoteness detection region.

7. The system according to claim 1, wherein:

at least one of the detection devices is configured to emit electromagnetic waves of a first frequency band for detecting the transponder and to be able to receive them from the transponder, and at least one of the detection devices is configured to be able to emit electromagnetic waves of a second frequency band for detecting the transponder and to be able to receive them from the transponder.

8. The system according to claim 1, wherein:

at least one of the detection devices is configured to emit electromagnetic waves according to a first transmission standard for detecting the transponder and to receive them from the transponder, and at least one of the detection devices is configured to emit electromagnetic waves according to a second transmission standard for detecting the transponder and to receive them from the transponder.

9. The system according to claim 8, wherein the monitoring network is configured to be operated according to a third transmission standard.

10. The system according to claim 1, wherein the monitoring network is partially or fully meshed.

11. The system according to claim 1, wherein at least one monitoring device is arranged in a sterile goods container.

12. The system according to claim 1, wherein:

at least one monitoring device is arranged in a storing region of a surgical environment, at least one monitoring device is arranged in the surgical environment in a sterile region at a side table in the vicinity of a surgical table, and at least one monitoring device is arranged in the surgical environment in the sterile region on the surgical table.

13. The system according to claim 1, further comprising a positioning system configured to be able to detect and/or register relative positions of the at least two monitoring devices.

14. A method for monitoring at least one medical product in a surgical environment, in which at least two monitoring devices connected or connectible to each other in a monitoring network in a data transmitting manner are arranged or arrangeable such that detection regions of the at least two monitoring devices extending around the respective monitoring device overlap, the method comprising the steps of:

detecting whether a transponder of the medical product is located in one of the detection regions;

storing of time points of detections of the transponder;

calculating time periods in which the transponder is located exclusively in one of the detection regions of the at least two monitoring devices; and comparing the calculated periods with corresponding stored target periods and outputting corresponding alarm signals when target periods are exceeded.

15. A method for monitoring at least one medical product in a surgical environment, in which at least two monitoring devices connected or connectible to each other in a monitoring network in a data transmitting manner are arranged or arrangeable such that detection regions of the at least two monitoring devices extending around the respective monitoring device overlap, the method comprising the steps of:

detecting whether a transponder of the medical product is located in one of the detection regions;

storing of time points of detections of the transponder;

registering sequences in which the at least two monitoring devices detect the transponder in the detection regions; and comparing the registered sequences with corresponding stored target sequences and outputting corresponding alarm signals in the event of a deviation from target sequences.

* * * * *